(12) United States Patent
Yasuda et al.

(10) Patent No.: US 7,092,154 B2
(45) Date of Patent: Aug. 15, 2006

(54) APPARATUS FOR MICROSCOPIC OBSERVATION OF LONG-TERM CULTURE OF SINGLE CELL

(75) Inventors: Kenji Yasuda, Tokyo (JP); Kunihiko Kaneko, Kanagawa (JP); Tetsuya Yomo, Osaka (JP); Ippei Inoue, Saitama (JP); Yuichi Wakamoto, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 10/432,396

(22) PCT Filed: Nov. 22, 2001

(86) PCT No.: PCT/JP01/10215

§ 371 (c)(1),
(2), (4) Date: Oct. 7, 2003

(87) PCT Pub. No.: WO02/42411

PCT Pub. Date: May 30, 2002

(65) Prior Publication Data
US 2004/0067482 A1 Apr. 8, 2004

(30) Foreign Application Priority Data
Nov. 22, 2000 (JP) .............................. 2000-356827

(51) Int. Cl.
*G01N 21/01* (2006.01)
*G02B 21/34* (2006.01)

(52) U.S. Cl. ...................... 359/398; 359/396; 356/244; 356/246

(58) Field of Classification Search ........ 359/396–398; 356/244, 246
See application file for complete search history.

(56) References Cited

U.S. PATENT DOCUMENTS

| 5,328,614 | A | * | 7/1994 | Matsumura | 210/632 |
| 6,216,538 | B1 | | 4/2001 | Yasuda et al. | |
| 6,287,765 | B1 | * | 9/2001 | Cubicciotti | 435/6 |
| 6,512,580 | B1 | * | 1/2003 | Behringer et al. | 356/244 |
| 2002/0173842 | A1 | * | 11/2002 | Okuzumi | 607/5 |

FOREIGN PATENT DOCUMENTS

JP  61-501126  6/1986

(Continued)

*Primary Examiner*—Drew A. Dunn
*Assistant Examiner*—Joshua L. Pritchett
(74) *Attorney, Agent, or Firm*—Wenderoth, Lind & Ponack, L.L.P.

(57) ABSTRACT

An apparatus is provided with a cell culture container having a cell culture region made of a hole formed on a substrate, a semi-permeable membrane covering a top plane of the cell culture region and a culture medium replacement part provided over the semi-permeable membrane, a mechanism for supplying a cell culture medium into the cell culture container, and a microscopic optical mechanism for enabling long-term observation of the cell within the cell culture region. This apparatus makes it possible to culture a cell group originating from a particular single cell, to perform culture and observation while identifying cells to be subjected to interaction during the process of culturing cells, and observe a difference in variation between the particular cell and other cells. There is also provided a mechanism which makes it possible to collect only a cell assuming a particular state and perform analysis or biochemical measurement of a gene of the cell, an expressed mRNA and the like.

30 Claims, 19 Drawing Sheets

FOREIGN PATENT DOCUMENTS

| | | |
|---|---|---|
| JP | 62-113698 | 7/1987 |
| JP | 1-248570 | 10/1989 |
| JP | 5-38281 | 2/1993 |
| JP | 7-47259 | 2/1995 |
| JP | 7-506430 | 7/1995 |
| JP | 9-289886 | 11/1997 |
| JP | 10-28576 | 2/1998 |
| JP | 11-56341 | 3/1999 |
| WO | 85/02201 | 5/1985 |
| WO | 93/22053 | 11/1993 |

* cited by examiner

APPARATUS FOR MICROSCOPIC OBSERVATION OF LONG-TERM CULTURE OF SINGLE CELL

TECHNICAL FIELD

The invention of the present application relates to an apparatus for the microscopic observation of long-term culture of a single cell. More specifically, the invention relates to an apparatus for microscopic observation of long-term culture of a cell, which enables the culturing of cells in units of one cell while observing the state of a particular cell microscopically, in the field of biotechnology that uses microorganisms and cells, as well as to a method of observation using such an apparatus.

BACKGROUND ART

Conventionally, in the fields of biology, medicine and pharmacy, changes in the state of a cell and the response of a cell to a certain drug has been observed on the assumption that the average value of a cell cluster represents the characteristic of one cell. However, in reality, cell cycles rarely synchronize with one another in a cell cluster and each of the cells expresses protein at a different cycle. Although synchronous culture methods have been developed in order to solve such problems, because the cultured cells do not originate from the exact same cell, there is a possibility that different protein expressions occur due to the difference between the genes of the individual pre-cultured cells. Hence, when the response to certain stimuli are actually analyzed, it is difficult to determine whether the fluctuation in the results are caused by the response fluctuation belonging generally to the cell response mechanism or from the difference between cells (i.e., the difference in genetic information between cells). In addition, since cell strains are not cultured from one cell, for similar reasons it is difficult to determine whether the reproducibility of response to stimuli fluctuate with the difference between the genes of individual cells. Furthermore, there are two kinds of stimuli (signals) to a cell: one that is given by the quantities of signal substances, nutrition and dissolved gases contained in the solution surrounding the cell, and one that is given by physical contact with other cells. Until recently, in the research field of biotechnology, observation of a cell was done by temporarily extracting part of a cell group cultured in a large culture unit and setting it in a microscope. Alternatively, microscopic observation was performed using a microscope enclosed in a temperature-controlled plastic container, which further contains a smaller container with means to control carbon dioxide concentration and humidity. In relation to such a method, various methods have been proposed for maintaining the solution conditions during cell culture by replacing the used medium with fresh medium. For example, in the method disclosed in JP-A-10-191961, a circulation pump operates to raise the level of the culture medium above the top edge of the substrate, or lower the level of the culture medium below the bottom edge of the substrate, and maintains a constant nutritional state by supplying fresh culture medium when the level of the culture medium is low, and discharging the culture medium when the level of the culture medium is high. Further, JP-A-8-172956 discloses a structure consisting of a culture container into which is inserted an insertion tube for introducing fresh culture medium into the culture container, an extraction tube for discharging culture medium from the culture container, and a gas tube which connects the gas phase of the culture container and the pump, each comprising a filter for preventing bacteria from entering the culture container, which can maintain the nutritional state of the culture container at a constant level.

However, in spite of these proposals, a method of culturing cells while controlling the solution conditions as well as physical contact between the cells has not yet been known. In addition, a means for selecting one particular cell and culturing the single cell as a strain is not known. Furthermore, the art of controlling solution conditions and cell density in a container, or the art of culturing and observing cells while identifying cells that interact with one another has not been known, either.

As is apparent from the foregoing description, in conventional technology, cell strains do not have the exact same gene because cell culture is initiated from a cell group. Further, in conventional technology, it is difficult to select particular cells and culture the selected cells while controlling the interaction or the density of the cells. Furthermore, in conventional technology, although attempts to maintain the solution condition by replacing the culture medium is being made, it is difficult to rapidly change the environment of a particular cell that is being cultured and observe the response of that cell.

Therefore, the subject of the present invention is to solve the above-described problems of the prior art, and to provide a novel technical means for enabling: the culture of a cell group originating from a particular single cell; the culture and observation of cells while identifying cells that interact with them; and the observation of the difference between a cell to which a substance that interacts with the cells, such as a signal substance, has been added, and other cells. The invention also aims to provide novel means which enables the collection of a cell that assumes a particular state and the analysis or biochemical measurement of a gene or an expression mRNA of the cell.

SUMMARY OF THE INVENTION

In order to solve the above-described problems, the present invention provides an apparatus for the microscopic observation of long-term culture of a single cell, which comprises: a cell culture container comprising a cell culture region consisting of a hole created on a substrate, a semi-permeable membrane covering the cell culture region and a culture medium exchange region on top of the semi-permeable membrane; a means for supplying liquid medium to the cell, culture container; and an optical microscopic means for long-term microscopic observation of a cell within the cell culture region.

In addition, the present invention provides various features of the form of such an apparatus. For example, in the above-described apparatus for microscopic observation of long-term culture of a single cell, a small culture container is set on the optical path of a microscopic observation system; the interior of the container comprises a cell culture region made of a small hole for culturing a cell, an optically transparent semi-permeable membrane that is coarse enough to prevent cells from passing through, which covers the top of the cell culture region to prevent the cell from coming out of the hole, and a culture medium exchange region that allows the culture medium to circulate on the top of the semi-permeable membrane. The cell culture region includes one or a plurality of small holes each having a width of approximately several μm to several hundred μm, and the apparatus has a means for guiding a particular cell to the hole. The apparatus also has a means for supplying nutrition and oxygen required for the growth of the cell in the cell culture region to the cell from the solution exchanging region by diffusion from the solution circulation part, which also enables excrements or secretion to be eliminated; and also has a means for optically observing the cell. In addition, the apparatus has a means for controlling the number and type of cells in each hole of the cell culture region by a non-contact trapping technique such as optical tweezers and a carrying passage formed between each hole.

The apparatus of the invention also has a means for controlling the solution temperature inside the container by temperate control means such as a Peltier element. Further, the feed tube for feeding culture medium from a culture medium reservoir to the solution exchanging region has a degassing means, such as a degassing cell or a gas replacement cell, as well as a means for controlling the type and density of gas dissolved in the culture medium.

Further, the apparatus of the present invention has a means for guiding the tip of a pipet or the like to the top of a particular hole and spraying a drug or the like to exert the influence of the drug on a single cell in the particular hole via the semi-permeable membrane, and a means for extracting one particular cell from a particular hole through the semi-permeable membrane by means of a pipet or the like, as well as a means for introducing a filler or the like into a particular hole by means of a similar pipet or the like.

Figure 1:
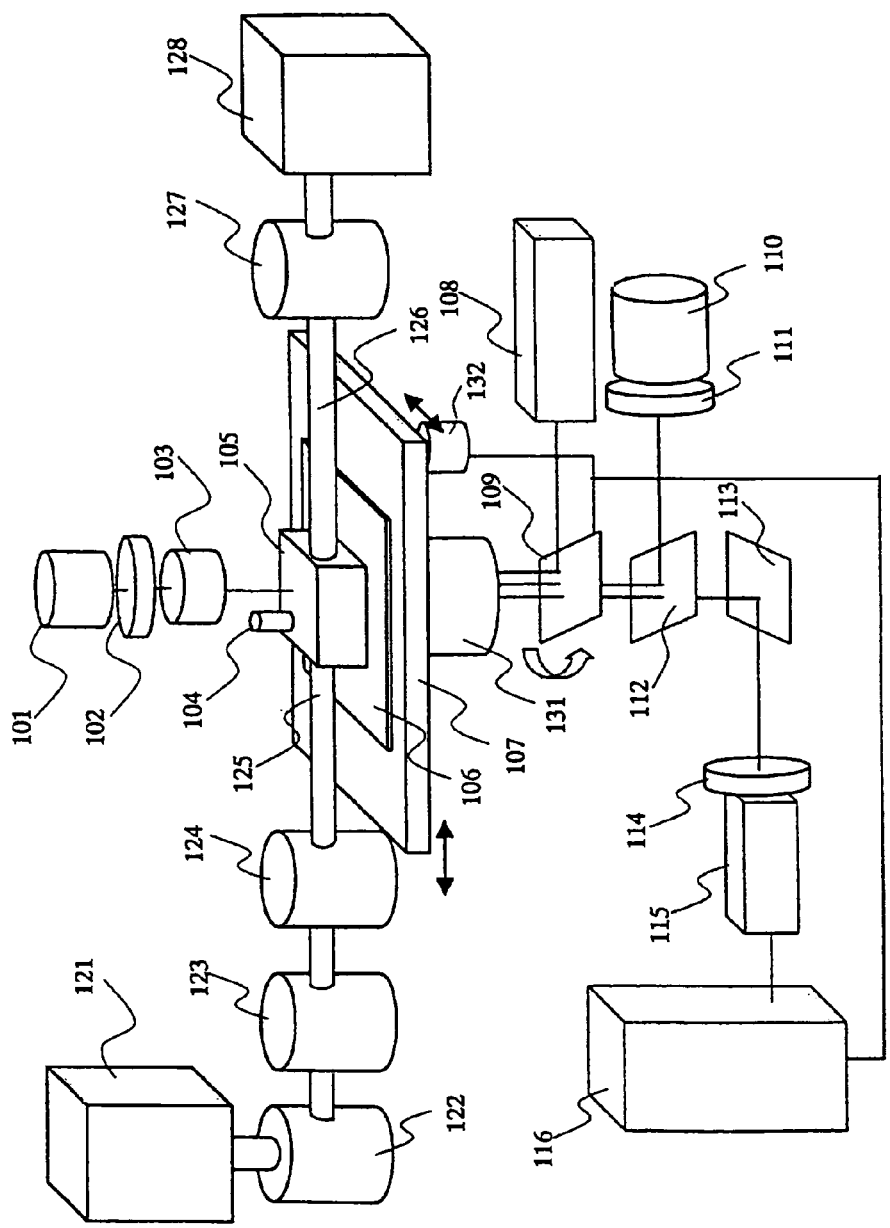
FIG. 1 is a schematic view showing an example of the basic construction of this invention.

101, 111 light source
102, 111 filter
103, 114 condenser lens
104 gas discharging valve
105 culture container
106 cell culture region substrate
107 stage having temperature control function
108 laser light source
109 movable dichroic mirror.
112 dichroic mirror
113 mirror
115 camera
116 image processing/analyzing and recording device
121 culture medium supplying device
122 heater
123 dissolved gas replacement device
124, 127 pump
125, 126 tube
128 waste solution reservoir
131 objective lens
132 stage moving motor
201 gas discharging value
202 culture container
203, 204 tube
301 culture container
301A solution exchanging region
302, 303 tube
304 semi-permeable membrane
305 cell culture region substrate
306 cell culture region
307 adhesive seal
401 semi-permeable membrane
402 cell culture region substrate
403 avidin
404 biotin
405 cell culture region
501 cell culture region substrate
502 cell culture region
502 cell
504 semi-permeable membrane
601 cell culture region substrate
602 cell culture region
701 cell culture region substrate
702, 703, 704, 705, 706 cell culture region
801 cell culture region substrate
802, 804 cell culture region
803, 805 cell
901 cell culture region substrate
902 cell culture region
903 groove
1001 cell culture region substrate
1002 cell culture region
1003 groove
1004 cell
1005 optical tweezers
1101 cell culture region substrate
1102 cell culture region
1103 groove
1104 cell reservoir
1202 cell culture region substrate
1202 sample introducing part
1203, 1205 cell trapping hole
1204, 1206 cell culturing hole
1207 groove
1208 cell observing hole
1301 culture container
1302, 1303 tube
1304 semi-permeable membrane
1305 cell culture region substrate
1306 hole -continued 1307 adhesive seal
1308 pipet
1311, 1314, 1317 flow of culture medium
1312 membrane of mineral oil
1313 culture medium
1315 solution level regulating part
1316 solution outlet
1401 cell culture region substrate
1402 hole
1403 cell
1404 semi-permeable membrane
1411 solution discharging pipet part
1412 solution sucking pipet part
1413 flow of pipet-discharged solution
1414 flow of pipet-sucked solution
1501 cell culture region substrate
1502, 1505, 1508 electrode
1503, 1506, 1509 hole
1504, 1507 groove
1510 moving direction of cell
1511, 1512 cell
1601 cell culture region substrate
1602, 1603 electrode
1604, 1605 ultrasonic vibrator
1611 direction of electric field
1612 direction of ultrasonic radiation pressure

BEST MODE FOR CARRYING OUT THE INVENTION

The invention of this application has features such as those described above, and embodiments of the invention will be described below.

First of all, it must be clearly pointed out that the term "one (single) cell" provided in the invention of this application must not be construed as limiting the number of cells to be handled at a time to only one call. A plurality of cells may be cultured in a hole of a cell culture region, and a feature of the invention of this application resides in the fact that even during the culture of a plurality of cells, it is possible to control and observe the culture process and the like of culture of a single particular cell. The term "one (single) cell" means that fact.

The term "long term" must not be construed as an absolute criterion, and is a relative criterion corresponding to the kind of each individual cell. In addition, it must be understood that longer-term control and observation of the culture process and the like can be realized than in any of the related art methods.

The invention of this application is based on the above-described premises.

FIG. 1 shows an example of the basic construction of an apparatus for microscopic observation of long-term culture. Referring to FIG. 1, the apparatus for microscopic observation of long-term culture according to the invention of this application is provided with a culture container 105 constructed to culture a microorganism or a cell and to enable replacement of its culture medium. The apparatus is also provided with a culture medium supplying and draining system which provides a culture medium while adjusting the composition and the temperature of a culture medium to be sent into the culture container 105, the kind and the density of gas and atmosphere, and the like, and an microscopic observation optical system for observing a cell in the culture container 105 with the lapse of time and recording the observed result on video or in a personal computer or the like.

More specifically, the culture container 105 in which to culture a cell is provided with a gas discharging valve 104 for discharging gases such as air remaining in the container, whereby the culture container 105 is structured to be filled with a culture medium. The size of the bottom of the culture container 105 is made to be a size suitable for microscopic observation. In addition, the culture container 105 is placed on a stage 107.

Referring to a culture medium supplying and draining part, the culture medium supplied from a culture medium supplying device 121 having the function of supplying a plurality of kinds of culture media or culture media having different densities to the culture container 105 is first adjusted in solution temperature by a heater 122, and is guided to a dissolved gas replacement device 123 via a tube and dissolved gas components such as air are adjusted by the dissolved gas replacement device 123. Then, the culture medium is adjusted in flow rate by a pump 124, and is sent to the culture container 105 via a tube 125.

The culture container 105 is provided with another tube 126, and the solution inside the culture container 105 passes through the tube 126 and is sent to a waste solution reservoir 128 by suction with a pump 127. The pump 124 and the pump 127, during observation, perform supply and drain of the culture medium of the culture container 105 at the same flow rate, but when the gas discharging valve 104 is in a closed state, either one of the pump 124 and the pump 127 can be omitted. The waste solution reservoir 128 is fitted with a heater so that the temperature of the culture medium can be adjusted, and by sending air or the like to a culture medium reservoir through a tube by a pump, it is also possible to bring the air contained in the culture medium into a saturated state.

The culture medium reservoir may be connected to the waste solution reservoir 128 via the tube so that a valve can be opened and closed to circulate the culture medium to a supplying device such as the culture medium supplying device 121. In this case, a filter may also be disposed in the tube at a halfway position thereof so that extra components can be removed from a waste solution.

The optical system with the basic construction shown in FIG. 1 is capable of illuminating a sample in two opposite directions, both from above and below. Light emitted from an upper light source 101 is adjusted to a particular wavelength by a filter 102, and is condensed by a condenser lens 103 and irradiated onto the culture container 105. The irradiated light is used as transmitted light for observation with an objective lens 131. A transmitted light image of the interior of the culture container 105 is guided to a camera 115 by a mirror 113 and forms an image on the photosensitive surface of the camera. Accordingly, the material of the culture container 105 and the material of a cell culture region substrate 106 for actually culturing a cell at the bottom of the culture container is desirably an optically transparent material. Specifically, glass such as borosilicate glass or quartz glass, resins or plastics such as polystyrene, or a solid substrate such as a silicon substrate is used. Particularly in the case where a silicon substrate is used, light of wavelength 900 nm or more is used for observation. Light irradiated from a lower light source 110 is guided to the objective lens 131 by a dichroic mirror 112 after having been wavelength-selected. The light is used as excitation light for observation of fluorescence in the interior of the culture container 105. Fluorescent light emitted from the culture container 105 is again observed with the objective lens 131, and only fluorescent light and transmitted light from which the excitation light has been cut by a filter 114 can be observed with the camera 115. At this time, by adjusting the combination of the filters 102, 111 and 114, it is possible to observe only transmitted light or only fluorescent light with the camera 115, or it is also possible to observe a transmitted light image and a fluorescent light image at the same time. In an optical path, a mechanism is also provided which introduces laser light generated by a laser light source 108 into the objective lens 131 through a movable dichroic mirror 109. In the case where this laser is used as optical tweezers, the focus position of the laser in the culture container 105 can be moved by moving the movable dichroic mirror. Image data obtained by the camera is analyzed by an image processing and analyzing device 116, and on the basis of various other analysis results such as the measured result of the temperature of a temperature measuring instrument attached to the culture container 105, it is possible to drive the movable dichroic mirror 109 as well as a stage moving motor 132 which causes the stage to move freely in the X-Y-Z directions in order to control the position of the stage having a temperature control function, on which the culture container 105 is placed. Accordingly, the shape of a cell can be recognized, and after recognition, the cell can be tracked and invariably positioned in the center of the image, or the image can be focused onto a particular cell by adjusting the distance to the objective lens. Otherwise, the movable dichroic mirror 109 and the stage 107 having a temperature control function, on which the culture container 105 is placed, can be controlled at a predetermined period, and the stage moving motor 132 can be driven at predetermined intervals.

Figure 2:
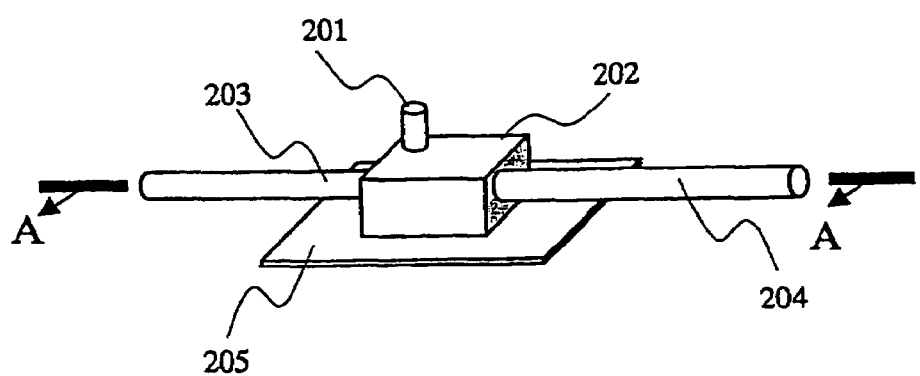
FIG. 2 is a schematic view showing the arrangement of the single-cell culture region shown in FIG. 1.
Figure 3:
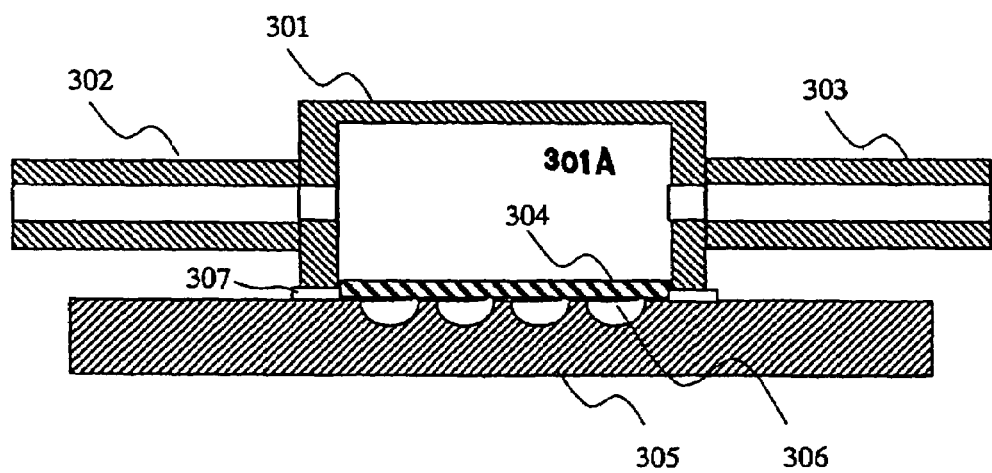
FIG. 3 is a schematic view showing an A—A cross section of the single-cell culture region shown in FIG. 1.
Figure 5:
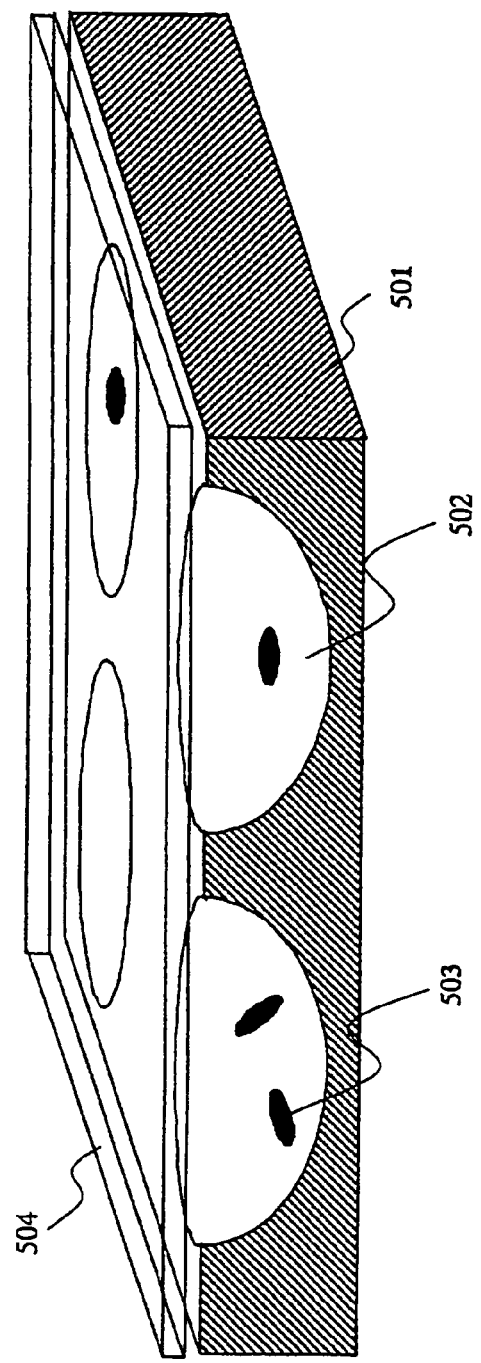
FIG. 5 is a schematic view showing the manner of cell trapping in the cell culture region.

FIG. 2 shows the arrangement of the culture container shown in FIG. 1. FIGS. 3 and 5 shot an A—A cross section of FIG. 2.

The culture container 202 shown in FIG. 2 is, similarly to the above-described container, provided with a gas discharging valve 201, a tube 203 for supplying a culture medium, and a tube 204 for discharging a waste solution, and a cell culture region substrate 205 similar to the cell culture region substrate 106 shown in FIG. 1 is provided at the bottom of the culture container 202.

The culture container 202 may be made of, for example, glass, but it is also possible to use various kinds of optically transparent containers made of a resin such as polypropylene or polystyrene, instead of glass.

In addition, it is possible to realize observation with near-infrared light of wavelength 900 nm or more by using a solid substrate such as a silicon substrate.

The cross-sectional view of FIG. 3 shows a culture container for cell culture according to the invention of this application as well as a construction with which this culture container is provided.

The culture medium supplied from the culture medium supplying device 121 shown in FIG. 1 described above is transferred into a solution exchanging region 301A of a culture container 301 via the tube 302 shown in FIG. 3. Then, the fresh culture medium stored in this solution exchanging region 301A is replaced with an old culture medium inside cell culture regions 306 via a semi-permeable membrane 304.

The cell culture regions 306 are made of a plurality of holes provided in a substrate 305. These holes are sealed at their tops by the semi-permeable membrane 304. Accordingly, the structure of the cell culture regions 306 is such that the cells sealed in the holes 306 cannot come out of these holes and unwanted microorganisms such as bacteria are prevented from entering from a culture medium part.

The size of each of these holes needs to be larger than the size of one cell. Accordingly, in general, in the case where a cell is to be cultured, the size of each of the holes, although depending on the size of the cell, can be made, for example, 3 mm or less in opening diameter and 300 µm in depth. More preferably, in order to advantageously achieve the expected object of the invention of this application, the opening diameter is set to from 1 µm to 1 mm, far more preferably, from 10 µm to 50 µm, and the depth is set to 100 µm or less. This opening diameter and depth may be appropriately adjusted according to the size and kind of cell to be cultured.

Regarding the height of the solution exchanging region 301A of the culture container 301, it in desirable that h be larger than the depth of the holes, in view of the diffusion of the culture medium.

In addition, regarding the thickness of the cell culture region substrate, it is necessary to use a thick substrate because an objective lens of high numerical aperture is used in the case where microscopic observation and optical trapping are performed with a 100-power objective lens. For example, in the case of a substrate made of borosilicate glass, it is necessary to use a substrate of thickness 0.3 mm or less.

The holes that constitute the cell culture regions 306 may be formed as a plurality of holes as described above, and in these holes, objective cells are cultured.

A waste solution of the culture medium is drawn from the solution exchanging region 301A through a tube 303. Since the holes of the cell culture regions 306 are very shallow, the replacement of the culture medium is rapidly performed, and the old culture medium is discharged through the tube 303.

The semi-permeable membrane 304 has micropores each having a size through which a cell cannot pass and an outside bacterium or the like cannot enter. In the invention of this application, more specifically, it is preferable that the semi-permeable membrane 304 be 10,000 or more in molecular weight MW, 0.2 µm or less in pore size, and optically transparent.

Since the semi-permeable membrane 304, as described above, has a pore size through which a cell cannot pass, unwanted microorganisms do not enter from the solution exchanging region 301A of the culture container 301 or cells do not flow into the solution exchanging region 301A from the holes of the cell culture regions 306.

The substrate 305 and the culture container 301, as shown in FIG. 3 by way of example, are made to adhere to each other by an adhesive seal 307 such as a silicone seal, whereby the culture medium is prevented from leaking from the solution exchanging region 301A. The substrate 305 is sealed by the semi-permeable membrane 304 with no clearance formed therebetween, except the tops of the holes of the cell culture regions 306. The reason for this is to disable a cell from moving between one and another of the holes in the case where the cell culture regions 306 are made of a plurality of holes.

Figure 4:
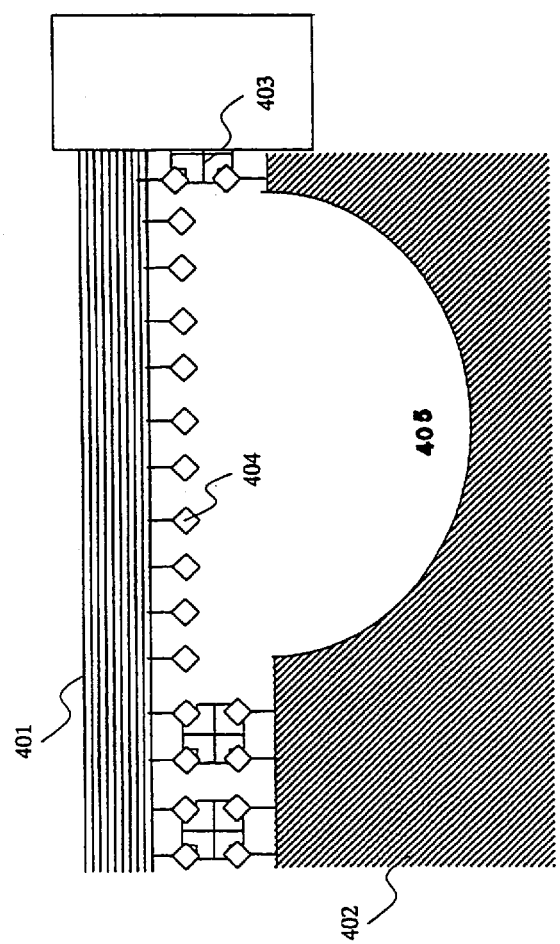
FIG. 4 is a schematic view showing one example of a method of bonding a substrate and a semi-permeable membrane.

As means for adhesion between the substrate 305 and the semi-permeable membrane 304, for example, a method using a bond between avidin and biotin is effective. FIG. 4 is a schematic cross-sectional view showing this bond. In the case where a cellulose membrane is used as a semi-permeable membrane 401 and glass is used as a substrate 402 of cell culture regions, the —OH group of the semi-permeable membrane 401 is partly converted to a —CHO group, and this is —(CO)—NH-bonded to biotin modified with an amino group. In this manner, the surface of the semi-permeable membrane 401 is modified with biotin 404. On the other hand, the surface of the glass substrate 402 is modified with an amino group by a silane coupling agent, and after that, the amino group is made to react with biotin having a —CHO group, whereby the surface of the substrate 402 can be modified with biotin similarly to the semi-permeable membrane. Then, avidin 403 is added to cause the semi-permeable membrane 401 to adhere to the cell culture region substrate 402 with a biotin-avidin bond.

In this manner, except the hole portion of a cell culture region 405, the biotin (404) disposed by bonding on the surface of one of the semi-permeable membrane 401 and the substrate 402 is bonded to the biotin (404) disposed by bonding on the surface of the other via the avidin 403, whereby a superior seal effect can be realized.

FIG. 5 is a schematic view showing the status of culture of cells 503 in the holes of cell culture regions 502 provided in a substrate 501. In accordance with culture according to the invention of this application, even in the case where, for example, a 60-power objective lens is used, the cells 503 in the holes of the cell culture regions 502 can be observed with a phase contrast microscope, a differential interference microscope or a fluorescence microscope similarly to the case of ordinary preparations. Incidentally, in FIG. 5, there is also shown a semi-permeable membrane 504.

Figure 6:
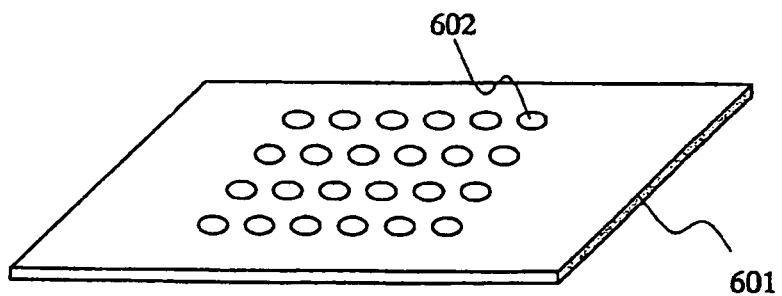
FIG. 6 is a schematic view showing one example of the structure of holes on a substrate surface.
Figure 7:
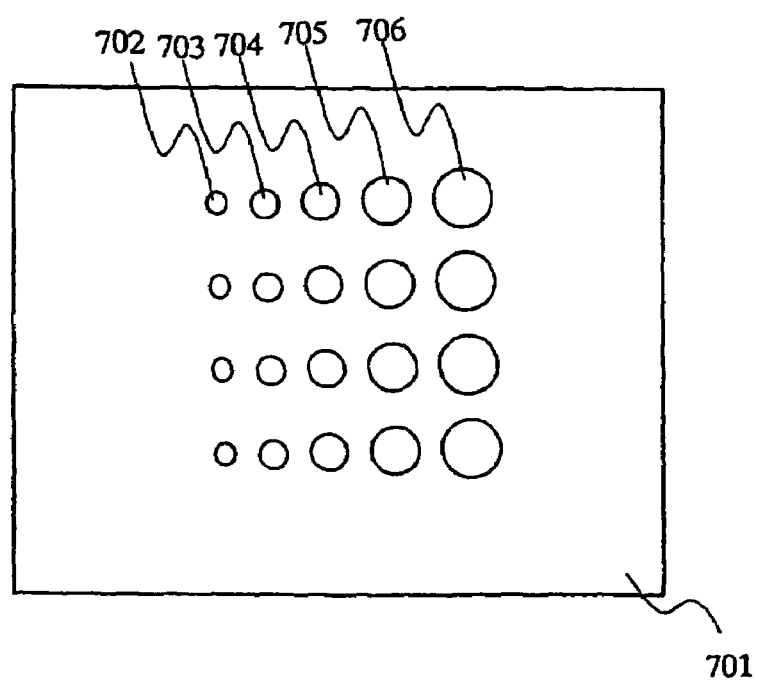
FIG. 7 is a schematic view showing one example of the structure of holes on a substrate surface.
Figure 8:
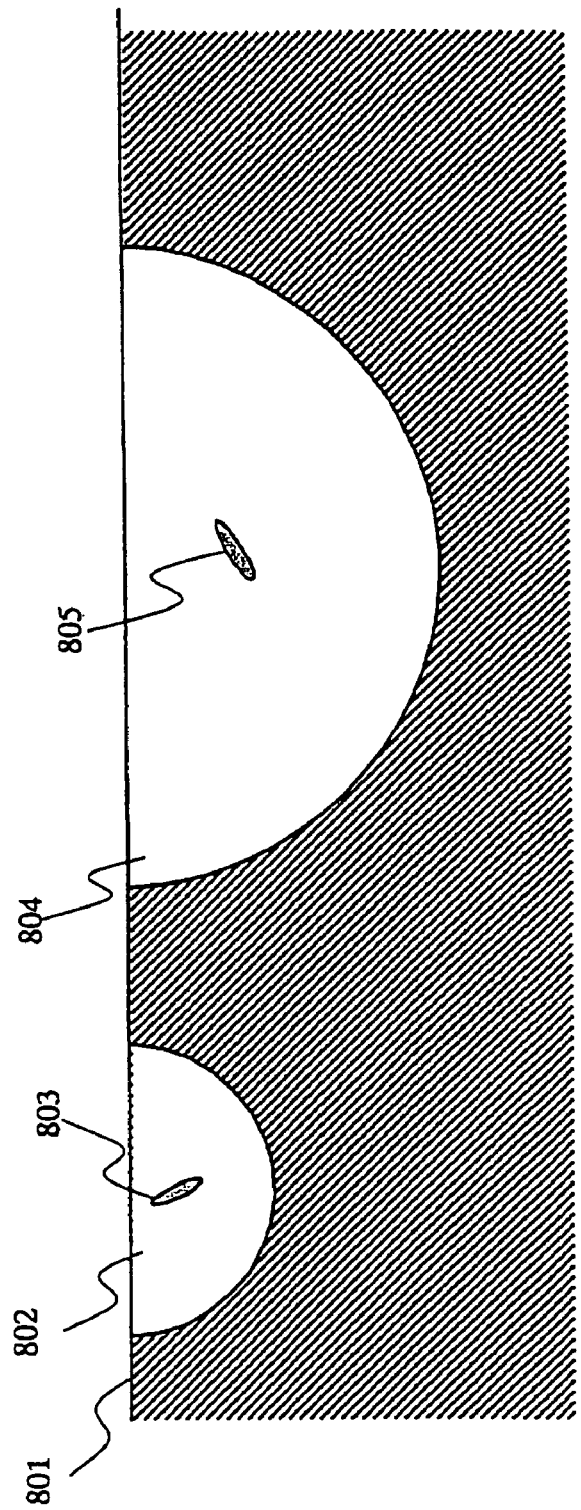
FIG. 8 is a schematic view showing the cross-sectional structures of the holes shown in FIG. 7 that have different sizes on a substrate surface.

Although bowl-shaped holes are shown in FIG. 5, various other shapes such as rectangles and polygons may also be used. As shown in FIG. 6 by way of example, holes which serve as cell culture regions may be of uniform or approximately uniform size and can be arranged on a substrate 601 as a plurality of cell culture regions 602 in the pattern of being spaced at equal intervals. Otherwise, as shown in FIG. 7, cell culture regions 702, 703, 704, 705 and 706 may be provided on the substrate 701 as holes which are gradually varied in size. FIG. 8 is a schematic view showing the status of culture of cells 803 and 805 in the holes of cell culture regions 802 and 804 having different sizes. At this time, the number of cells in each of the holes is one, but the holes differ from each other in cell density which is obtained by dividing the number of cells in a hole by the volume of the hole. In this manner, by controlling the volume of each hole, it is possible to observe various reactions of the same number of cells for different densities.

It goes without saying that the arrangement pattern and number of holes which serve as cell culture regions, as well as the sizes and shapes of the holes may be suitably determined.

According to the invention of this application, for example, by changing the size (diameter) of a hole of a cell culture region, it is possible to change the extent of the mean free path of a cell which is an objective target, or by changing the number of objective target cells to be placed into holes of the same size (diameter), it is possible to change the cell density of each of the holes. In addition, if the shape of a hole for cell culture is changed, it is possible to observe the influence and effect of the shape on a cell.

Figure 9:
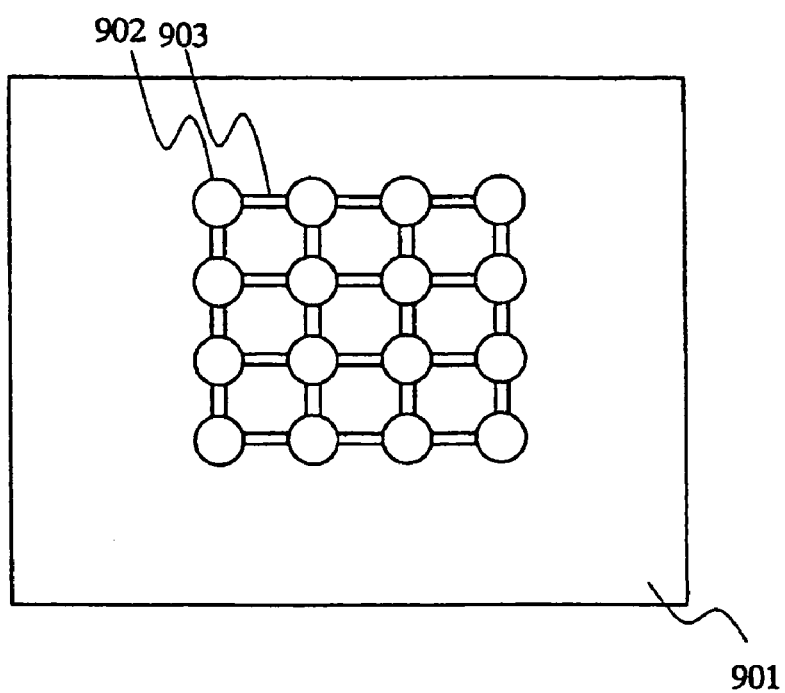
FIG. 9 is a schematic view showing one example of the structures of holes on a substrate surface.

According to the invention of this application, as shown in FIG. 9 by way of example, a plurality of holes serving as cell culture regions 902 and grooves 903 interconnecting these holes and serving as thin passages each of which allows one cell to narrowly pass therethrough may be provided on the surface of a substrate 901. By providing the grooves 903 serving as such passages, it is possible to measure, for example, the moving velocity, runnability and the like of cells. In addition, it is possible to transfer a cell from each of the cell culture region holes to an adjacent one via a passage by using particle trapping means such as optical tweezers. By using optical tweezers, it is possible to isolate or select cells, and it is possible to cause particular cells to interact with one another in a hole, as well as it is possible to control the number of cells in a hole.

Figure 10:
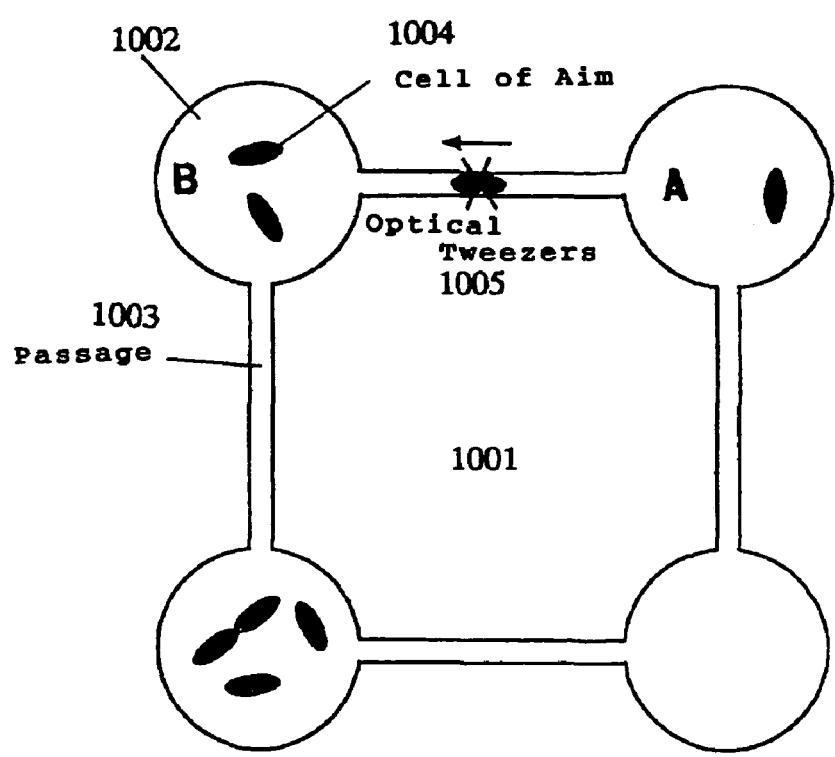
FIG. 10 is a schematic view explaining means for carrying a cell by using optical tweezers from one to another one of the holes shown in FIG. 9.

FIG. 10 is a schematic plan view showing the manipulation of such cell movement. Holes serving as cell culture regions 1002 and grooves 1003 serving as passages for interconnecting these holes are provided in a substrate 1001, and a cell 1004 can be moved through the groove 1003 from a hole A to another hole B of the cell culture regions 1002 by optical tweezers 1005 means. The optical tweezers 1005 means in this case is means which has heretofore been well known, and is means for irradiating a target cell with a beam of laser light to trap the cell and enabling the cell to be moved in its trapped state with the movement of the beam of laser light.

Figure 11:
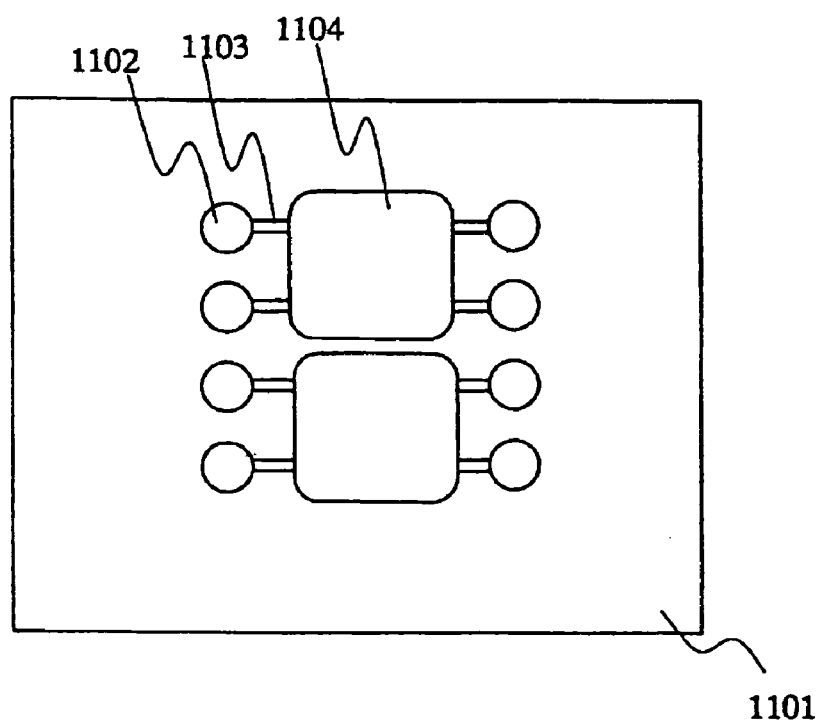
FIG. 11 is a schematic view showing one example of the structures of holes on a substrate surface.
Figure 12:
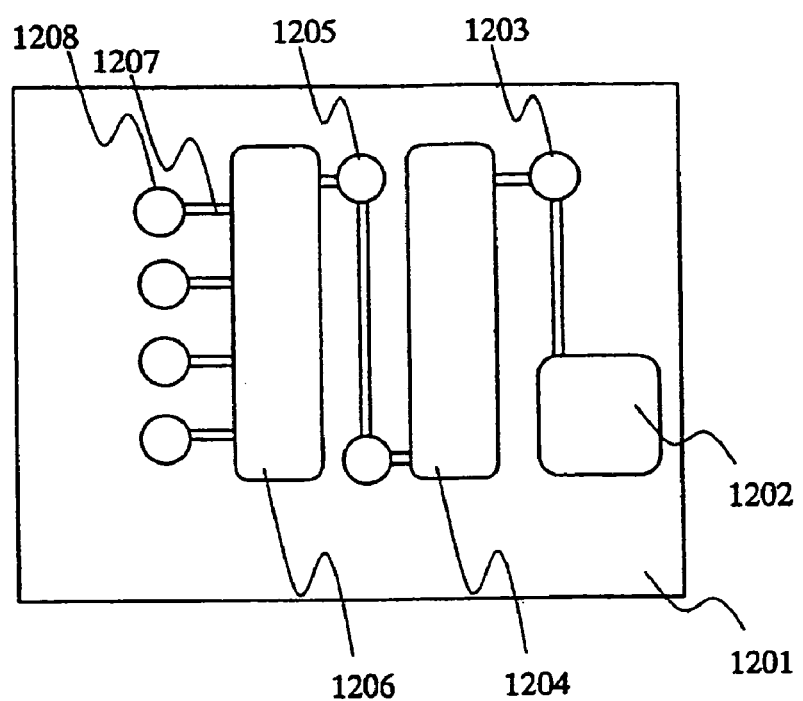
FIG. 12 is a schematic view showing one example of the structures of holes on a substrate surface.

According to the means of the optical tweezers 1005, as shown in FIG. 11 by way of example, in a structure in which a hole of a cell culture region 1102 provided in a substrate 1101 and a hole of a cell reservoir 1104 are made to communicate with each other by a groove 1103 which serves as a passage, a particular cell can be carried from the hole of the cell reservoir 1104 to the hole of the cell culture region 1102 by the optical tweezers, and conversely, a particular cell can also be transferred or discarded into the hole of the cell reservoir 1104. Otherwise, as shown in FIG. 12 by way of example, a single-cell purification culture system can also be assembled on a cell culture region substrate 1201. In this case, first of all, cells are introduced into a sample introducing part 1202, and one of these cells is moved along a groove by the use of trapping means such as optical tweezers, and is guided to a cell culturing hole 1204. A cell trapping hole 1203 is disposed in this groove at a halfway position thereof to prevent a cell from swimming from 1202 into a hole 1204. Then, one cell which is in a particular state is again taken out of a cell group cultured and grown from the one cell in the hole 1204, and this cell is similarly moved by the use of the trapping means, and is guided to a second culturing hole 1206. Similarly, a cell trapping hole 1205 is disposed at a halfway position. When the cell cultured in the hole 1206 grows to assume a certain predetermined state, cells are carried to a cell observing hole 1208 through a cell carrying groove 1207, and observation or the like is performed.

Figure 13:
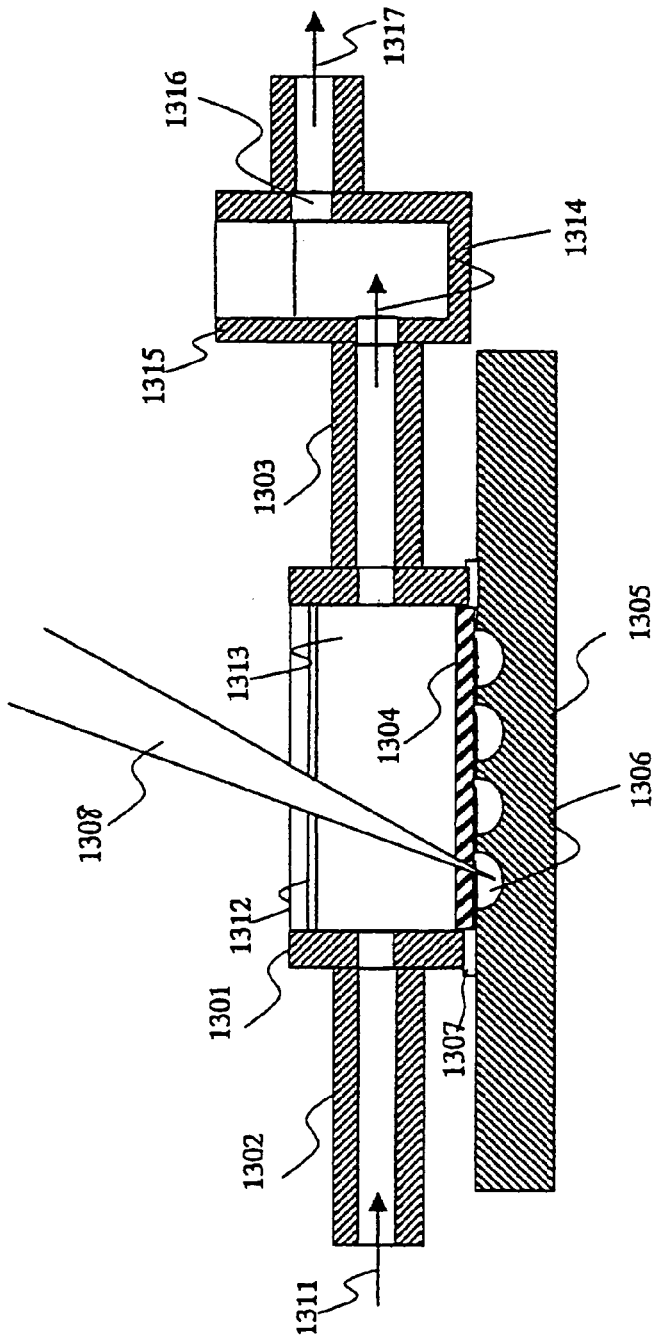
FIG. 13 is a schematic view showing one example of the construction of a cell culture region.

FIG. 13 shows one example of a culture container different from the embodiment shown in FIG. 2. In this example, a pipet 1308 is introduced from the outside, and is inserted through a semi-permeable membrane 1304 to selectively collect cells in a hole 1306. For this reason, a culture container 1301 is made open at its top, and a mineral oil 1312 is applied to cover the top surface of a culture medium 1313 with which the container is filled, thereby preventing the penetration of unwanted microorganisms. The amount of the culture medium to be introduced through a tube 1302 in the direction of an arrow 1311 is made smaller than the amount of solution to be sucked in the direction of an arrow 1317, and by the use of a solution level regulating part 1315, when this solution level becomes lower than a solution outlet 1316, air is sucked to stop the suction of solution, and when the solution level becomes higher to close the outlet 1316, the culture medium is again sucked, so that the solution level is held at a constant height. In this example, the solution level regulating part is installed separately from the culture container 105 so that ripples on a solution surface do not influence optical observation. The pipet 1308 can be used for sucking a cell, but can also be used for injecting a filler to close a particular hole or groove or for introducing a particular cell into a cell culture region through a semi-permeable membrane. For example, the pipet 1308 can be used in the case of introducing a particular sample into the sample introducing part 1202 of the single-cell purification culture system shown in FIG. 12. At this time, it is possible to experiment the cell introduced by the pipet without any problem of contamination, by moving the cell along the groove toward the hole sealed with the semi-permeable membrane, by trapping means such as optical tweezers before other cells or the like penetrate through a cut in the semi-permeable membrane. In addition, in the embodiment, since cells which assume a particular state can be collected in units of one cell with a pipet 1, gene polymorphism analysis, mRNA expression analysis and the like can be also performed on this one cell.

Figure 14:
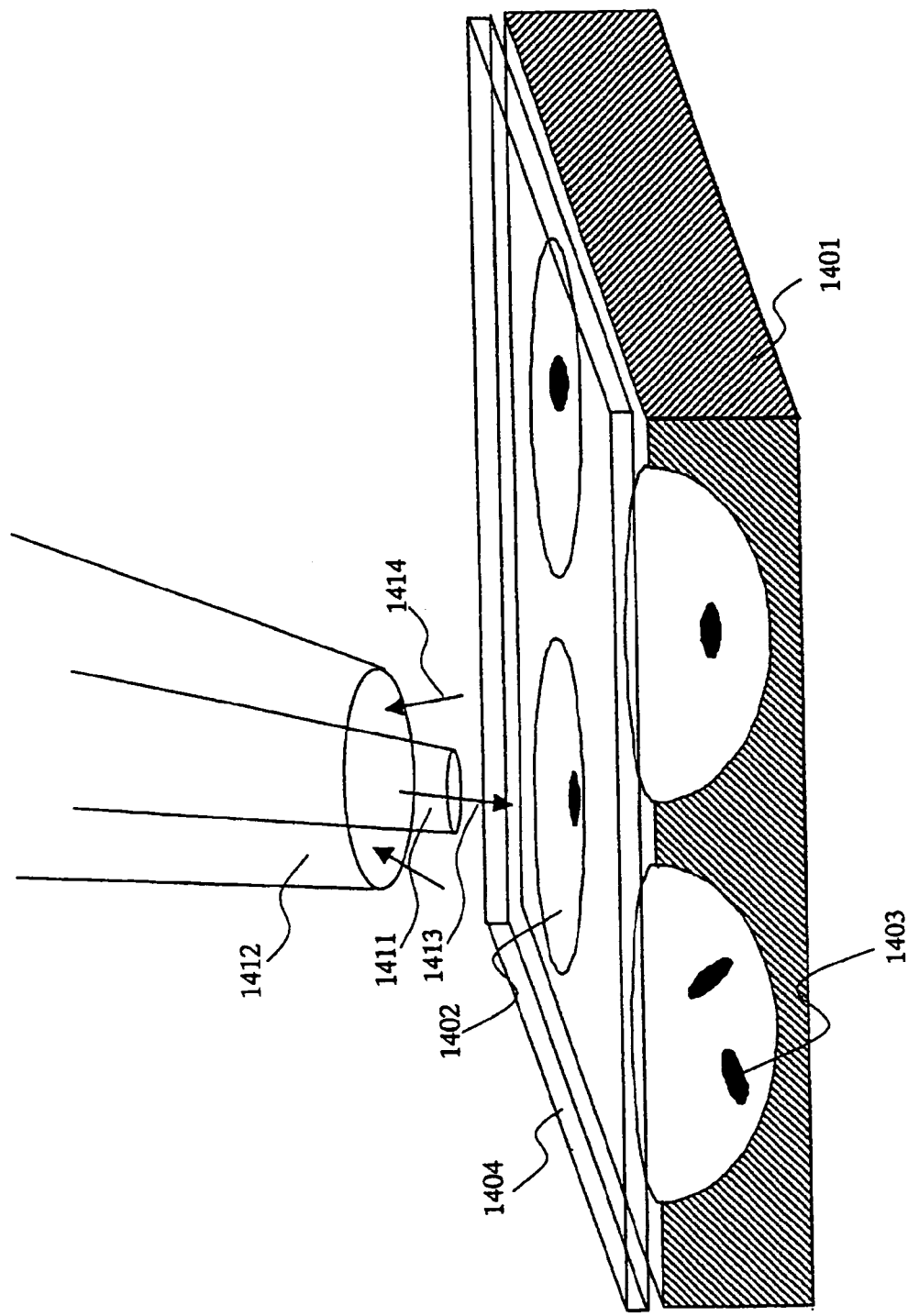
FIG. 14 is a schematic view showing one example of the construction of a cell culture region.

FIG. 14 shows an embodiment in which a reagent for causing induction or the like is introduced into a cell in a particular hole 1402. In this case, a pipet has a double structure, and discharges a solution through an inside pipet 1411 and sucks a solution through an outside pipet 1412. Accordingly, the structure of the pipet is such that the solution discharged from the inside pipet 1411 is distributed in the vicinity of only its outlet and is prevented from leaking outwardly from the outside pipet 1412, by suction from the outside pipet 1412. Accordingly, this pipet can be brought to the vicinity of a particular hole and apply an action to only a particular cell.

Incidentally, owing to the movement of cells by trapping and moving means such as the above-described optical tweezers according to the invention, it is possible to control the density of particular cells in a hole of a cell culture region, and it is also possible to implement identification of cells which interact with one another, control of the time period of interaction, and the like. However, the cell trapping and moving means is not limited to the above-described optical tweezers, and may also be, for example, means using ultrasonic waves or means using electric fields.

Figure 15:
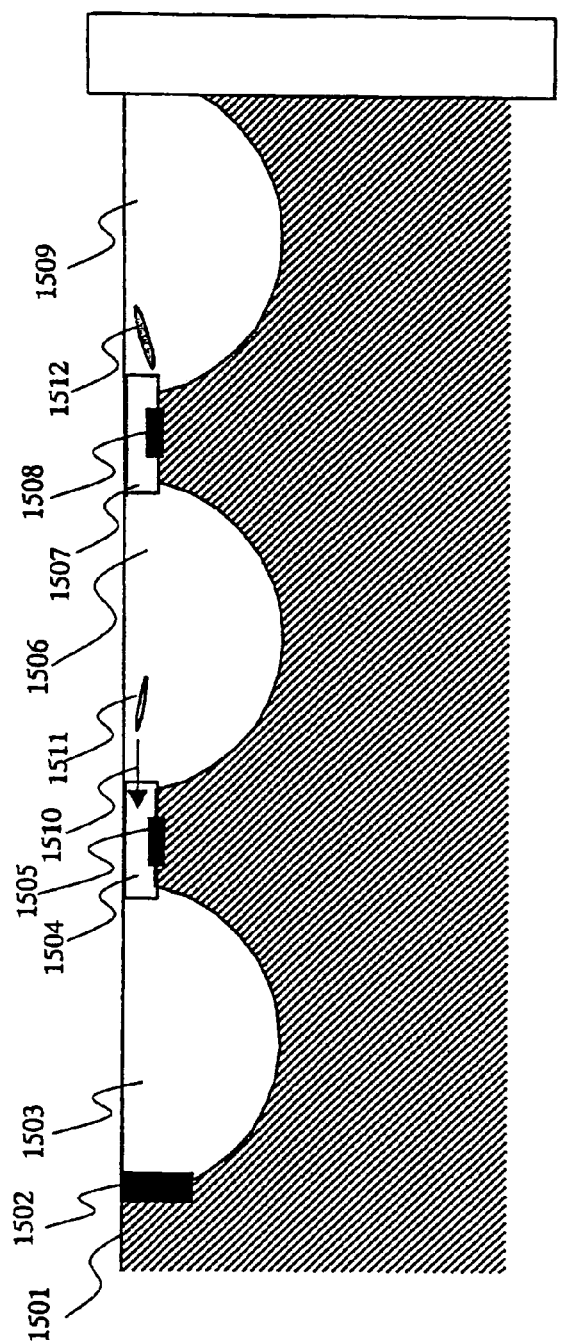
FIG. 15 is a schematic view showing one example of the structures of holes on a substrate surface.

FIG. 15 shows one embodiment in which a plurality of electrodes 1502, 1505 and 1508 are introduced in a cell culture region substrate 1501. Since a cell has a peculiar charge in a solution according to the state of the surface thereof, when a positive charge is applied to an electrode 1502, a cell 1511 having the opposite charge can be attracted to a hole 1503. By using this technique, cells corresponding to different strengths of negative charges are gathered in the hole 1503 and holes 1506 and 1509, respectively. In addition, if negative charges are applied to the electrodes 1505 and 1508, cells cannot move between each of the holes.

Figure 16:
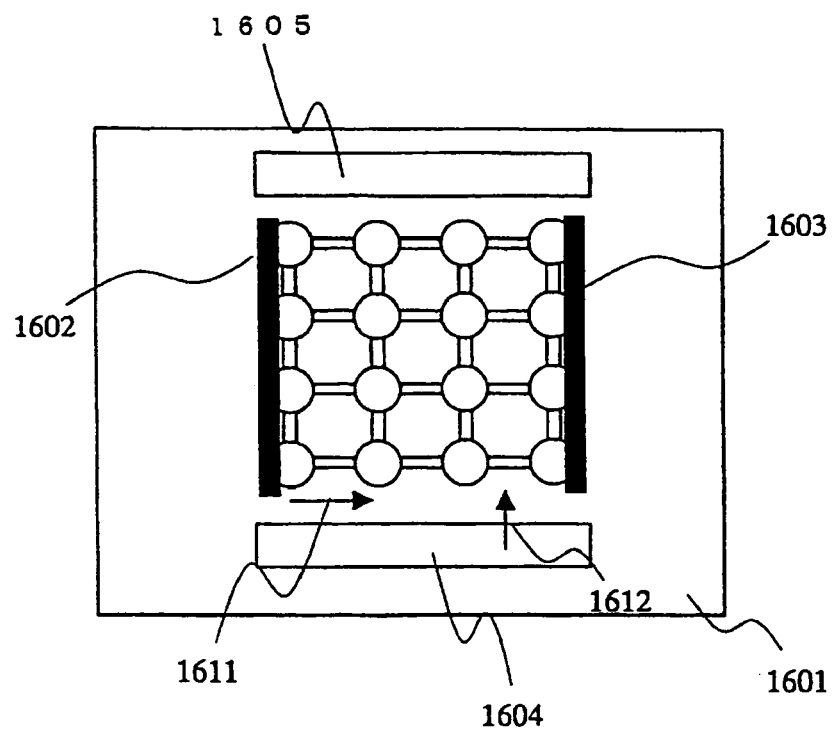
FIG. 16 is a schematic view showing one example of the structures of holes on a substrate surface.

FIG. 16 shows one example in which electrodes 1602 and 1603 are disposed on a cell culture region substrate 1601 and ultrasonic vibrators 1604 and 1605 are disposed. In this example, an electric field 1611 and an ultrasonic radiation pressure 1612 are used as non-contact forces for manipulating a cell. The electric field applies to a cell an external force corresponding to the surface charge of the cell, while the ultrasonic radiation pressure exerts over the cell an external force corresponding to the size and hardness of the cell. It is desirable that the frequency of an ultrasonic wave to be used at this time be made a frequency of 1 MHz or more so that the generation of bubbles (cavitation) can be restrained. In this embodiment, specifically, the ultrasonic radiation pressure and the electric field are respectively made to act in different directions perpendicular to each other, whereby cell distribution corresponding to the charge and size of each cell can be two-dimensionally developed. In addition, in this example, an external force due to an electric field and an external force due to an ultrasonic wave are combined on one substrate to perform separation according to the kinds of cells, but external forces due to an electric field and an ultrasonic wave may also be independently used to transport a cell. Accordingly, it is possible to achieve cell handling similar to that used with optical tweezers.

In the invention of this application, it is possible to provide means for measuring the number of cells in a hole serving as a cell culture region, and further, it is possible to provide a pipet which can be inserted into a hole of a cell culture region through a semi-permeable membrane and collect a particular cell in the hole or inject or collect a reagent or a filler in the hole. It goes without saying that various other detailed practical forms can be used without being limited to any of the above-described forms.

For example, as described above, in the apparatus for microscopic observation of long-term culture of a single cell according to this application, it is possible to obtain, for example, the following superior advantages.

(1) A particular cell can be isolated and observed for a long time.

(2) The kind and the temperature of a culture medium can be freely changed during culture.

(3) The volume and the shape of a culture container can be freely set.

(4) The number of cells being cultured can be accurately set during culture.

(5) Other unwanted microorganisms do not enter a container in which cells are being cultured.

Figure 17:
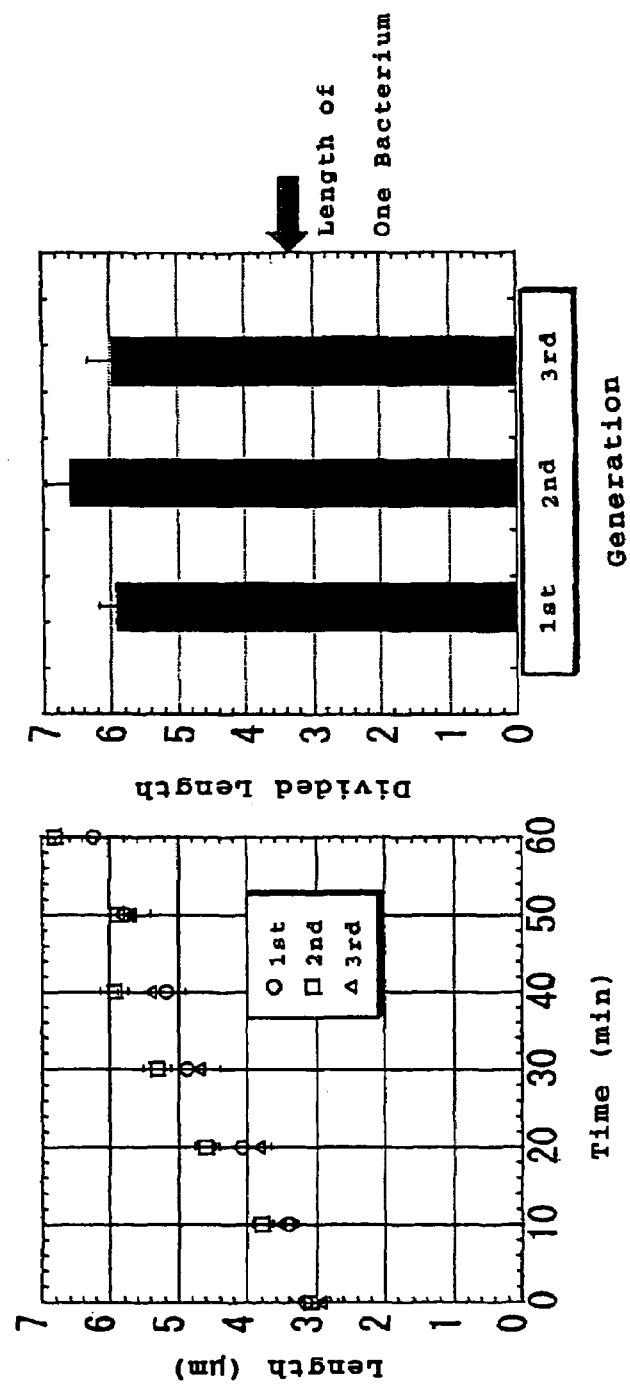
FIG. 17 is a view showing the result of observation of the growth speed and division length of each generation of *E. coli*.
Figure 18:
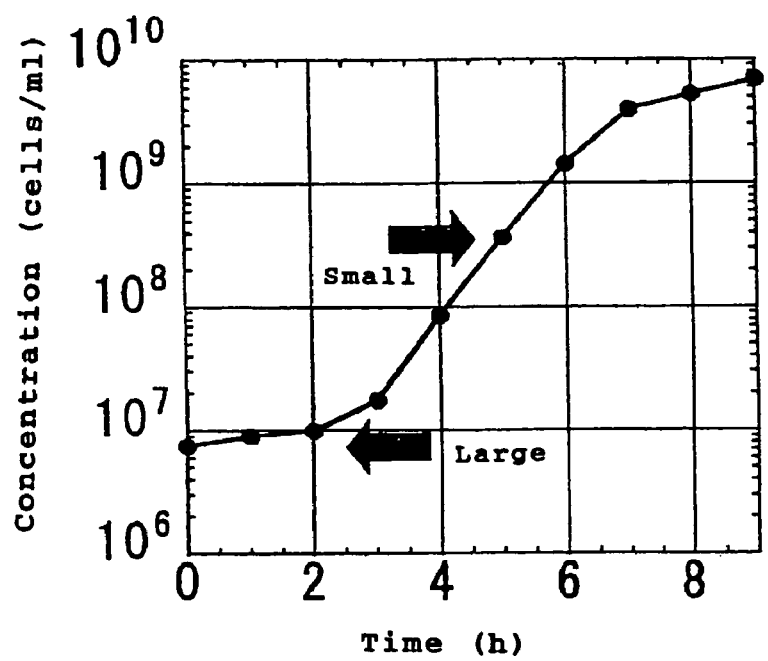
FIG. 18 is a view showing the result of observation of the volume dependence of growth of *E. coli*.

By using the above-described apparatus of this application, as shown in FIG. 17 by way of example, in an observation of *E. coli* growth, it has been confirmed that there is no difference in growth speed and division length between each generation and one *E. coli* bacterium divides into two when reaching a two-fold length. On the other hand, as shown in FIG. 18, it has been confirmed that growth depends on the size, i.e., the volume, of a hole of a cell culture region. In FIG. 18, "larger" indicates $2 \times 10^{-7}$ ml, and "small" indicates $2 \times 10^{-9}$ ml.

Figure 19:
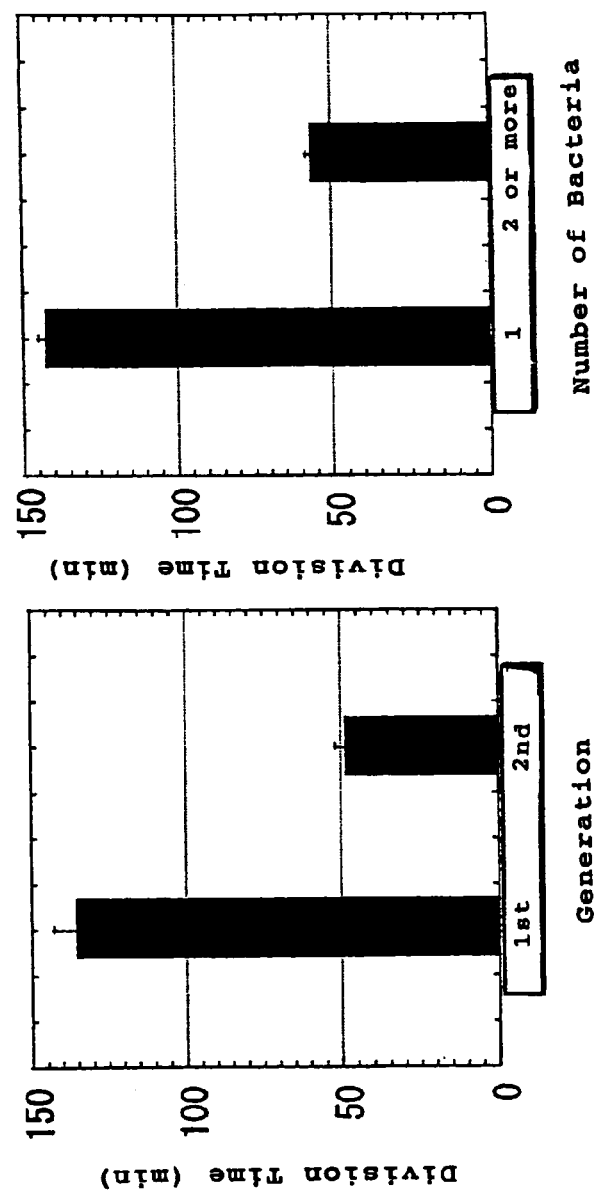
FIG. 19 is a view showing the result of observation of the difference in division time between generations of *E. coli* and the difference in division time between the initial numbers of bacteria during division of *E. coli*. Incidentally, the reference numerals used in the drawings are as follows.

As shown in FIG. 19, there is a difference in division time between generations and between the numbers of initial bacteria, and it has been confirmed that the first division takes time until the beginning of division and one cell takes a long time until the beginning of division compared to the case of a plurality of cells.

This feature can be realized exclusively by the apparatus and the method according to the invention of this application which enables long-term culture and microscopic observation at the level of a single cell.

INDUSTRIAL APPLICABILITY

As described hereinabove in detail, according to the invention of this application, by solving the problem of the related art, there is provided novel technical means which makes it possible to culture a cell group originating from a particular single cell, to perform culture and observation while identifying cells to be subjected to interaction during the process of culturing cells, to spray a substance which interacts with cells, for example, a drug such as a signal substance, onto only a particular cell in a cell group which is being cultured so that cells are cultured at a constant cell density, and observe a difference in variation between the particular cell and other cells. According to the invention of this application, there is also provided novel means which makes it possible to collect only a cell assuming a particular state and perform analysis or biochemical measurement of a gene of the cell, an expressed mRNA and the like.

The invention claimed is:

1. An apparatus for enabling isolation, long-term culture and observation of a cell, said apparatus comprising:
   a cell culture container having a culture medium exchange region;
   a culture medium supplying device that supplies culture medium to said cell culture container;
   a substrate coupled to said cell culture container;
   a first cell culture region formed in said substrate, said first cell culture region comprising a first hole and being formed to hold one or more cells therein;
   a second cell culture region formed in said substrate, said second cell culture region comprising a second hole and being formed to hold one or more cells therein;
   a semi-permeable membrane arranged so as to cover said first cell culture region and said second cell culture region; and
   a groove formed in said substrate,
   wherein said groove connects said first cell culture region to said second cell culture region, and serves as a thin passage for a cell such that the cell can pass between said first cell culture region and said second cell culture region, and
   wherein said culture medium exchange region is disposed above said semi-permeable membrane.

2. The apparatus according to claim 1, further comprising:
   a first electrode disposed in a vicinity of said first cell culture region; and
   a second electrode disposed in a vicinity of said second cell culture region;
   wherein, when a charge is applied to said first electrode, a cell disposed within said second cell culture region moves from said second cell culture region to said first cell culture region via said groove that connects said first cell culture region to said second cell culture region.

3. A method for the microscopic observation of long-term culture of a single cell, which comprises the use of the apparatus of claim 2.

4. The apparatus according to claim 1,
   wherein each of said first cell culture region and said second cell culture region have a diameter larger than or equal to 1 μm and smaller than or equal to 1 mm, and a depth less than or equal to 100 μm, and
   wherein said semi-permeable membrane has a molecular weight of 10,000 or more and a pore size of 0.2 μm or smaller.

5. A method for the microscopic observation of long-term culture of a single cell, which comprises the use of the apparatus of claim 4.

6. The apparatus according to claim 1, wherein said cell culture container is made of an optically transparent material.

7. A method for the microscopic observation of long-term culture of a single cell, which comprises the use of the apparatus of claim 6.

8. The apparatus according to claim 1, wherein said semi-permeable membrane is fixed to a top surface of said substrate by avidin-biotin bonding.

9. A method for the microscopic observation of long-term culture of a single cell, which comprises the use of the apparatus of claim 8.

10. The apparatus according to claim 1, wherein said cell culture container further comprises a draining mechanism, so that the culture medium supplied to said culture medium exchange region from said culture medium supplying device is exchanged with used culture medium in said first and second cell culture regions through said semi-permeable membrane, wherein the used culture medium is discharged by said draining mechanism.

11. A method for the microscopic observation of long-term culture of a single cell, which comprises the use of the apparatus of claim 10.

12. The apparatus according to claim 1, further comprising a valve operable to discharge gas remaining in said cell culture container.

13. A method for the microscopic observation of long-term culture of a single cell, which comprises the use of the apparatus of claim 12.

14. The apparatus according to claim 1, further comprising a mechanism for controlling a temperature of the culture medium.

15. A method for the microscopic observation of long-term culture of a single cell, which comprises the use of the apparatus of claim 14.

16. The apparatus according to claim 1, wherein the cell can be trapped and moved between said first cell culture region and said second cell culture region by an optical tweezers.

17. A method for the microscopic observation of long-term culture of a single cell, which comprises the use of the apparatus of claim 16.

18. The apparatus according to claim 1, wherein the cell can be tapped and moved between said first cell culture region and said second cell culture region by an ultrasonic wave.

19. A method for the microscopic observation of long-term culture of a single cell, which comprises the use of the apparatus of claim 18.

20. The apparatus according to claim 1, wherein the cell can be trapped and moved between said first cell culture region and said second cell culture region by an electric field.

21. A method for the microscopic observation of long-term culture of a single cell, which comprises the use of the apparatus of claim 20.

22. The apparatus according to claim 1, wherein a pipet can be utilized for spraying reagents into said first cell culture region and said second cell culture region and for collecting the reagents.

23. A method for the microscopic observation of long-term culture of a single cell, which comprises the use of the apparatus of claim 22.

24. The apparatus according to claim 1, further comprising:
   an optical microscope which enables long-term microscopic observation of a cell within said first cell culture region or said second cell culture region; and
   a filter inserted into an optical path of said optical microscope so as to enable fluorescence observation of the cell.

25. A method for the microscopic observation of long-term culture of a single cell, which comprises the use of the apparatus of claim 24.

26. The apparatus according to claim 1, further comprising:
   a means for acquiring image data;
   a means for recognizing a shape of a particular cell in the image data; and a means for controlling a position of a stage and a focal length of an objective lens so as to maintain the particular cell in a center of a visual field.

27. A method for the microscopic observation of long-term culture of a single cell, which comprises the use of the apparatus of claim 26.

28. The apparatus according to claim 1, further comprising a means for measuring the number of cells in said first and second cell culture regions.

29. A method for the microscopic observation of long-term culture of a single cell, which comprises the use of the apparatus of claim 28.

30. A method for the microscopic observation of long-term culture of a single cell, which comprises the use of the apparatus of claim 1.

* * * * *